US011690936B2

(12) United States Patent
Fawdry et al.

(10) Patent No.: US 11,690,936 B2
(45) Date of Patent: Jul. 4, 2023

(54) CELL ENCAPSULATION MEMBRANES, DEVICES AND METHODS

(71) Applicant: Boston Scientific Limited, Hamilton (BM)

(72) Inventors: Martin Lawrence Fawdry, Galway (IE); Aiden Flanagan, Kilcolgan (IE); Matthew McEvaddy, Galway (IE); Garry Duffy, County Kildare (IE); Eamonn J. Tuohy, Thurles (IE)

(73) Assignee: Boston Scientific Limited, Hamilton (BM)

( * ) Notice: Subject to any disclaimer, the term of this patent is extended or adjusted under 35 U.S.C. 154(b) by 2 days.

(21) Appl. No.: 17/222,634

(22) Filed: Apr. 5, 2021

(65) Prior Publication Data

US 2021/0220524 A1 Jul. 22, 2021

Related U.S. Application Data

(62) Division of application No. 15/717,201, filed on Sep. 27, 2017, now Pat. No. 10,967,102.

(60) Provisional application No. 62/400,754, filed on Sep. 28, 2016.

(51) Int. Cl.
| | |
|---|---|
| *A61L 27/56* | (2006.01) |
| *A61M 31/00* | (2006.01) |
| *A61L 27/38* | (2006.01) |
| *A61L 27/30* | (2006.01) |
| *A61L 27/52* | (2006.01) |
| *A61L 27/34* | (2006.01) |
| *A61L 27/54* | (2006.01) |

(52) U.S. Cl.
CPC ............... *A61L 27/56* (2013.01); *A61L 27/30* (2013.01); *A61L 27/34* (2013.01); *A61L 27/38* (2013.01); *A61L 27/52* (2013.01); *A61L 27/54* (2013.01); *A61M 31/002* (2013.01); *A61L 2300/412* (2013.01); *A61L 2300/414* (2013.01); *A61L 2300/62* (2013.01); *A61L 2300/64* (2013.01); *A61L 2420/04* (2013.01)

(58) Field of Classification Search
CPC .......... A61L 27/56; A61L 27/30; A61L 27/34; A61L 27/38; A61L 27/52; A61L 27/54; A61L 31/002; A61L 2300/412; A61L 2300/414; A61L 2300/62; A61L 2300/64; A61L 2420/04
See application file for complete search history.

(56) References Cited

U.S. PATENT DOCUMENTS

| | | | |
|---|---|---|---|
| 8,636,753 B2 | 1/2014 | Buevich et al. | |
| 8,771,734 B2 | 7/2014 | Tabata | |
| 9,011,899 B2 | 4/2015 | Haworth et al. | |
| 10,967,102 B2 | 4/2021 | Fawdry et al. | |
| 2004/0022939 A1 | 2/2004 | Kim et al. | |
| 2005/0055075 A1 | 3/2005 | Pinchuk et al. | |
| 2005/0118236 A1 | 6/2005 | Qiu et al. | |
| 2008/0033522 A1 | 2/2008 | Grewe et al. | |
| 2008/0086216 A1 | 4/2008 | Wilson et al. | |
| 2012/0185004 A1 | 7/2012 | McJames et al. | |
| 2012/0276188 A1* | 11/2012 | Barrows | A61L 27/3834 424/443 |
| 2014/0275905 A1 | 9/2014 | Klueh et al. | |
| 2015/0297798 A1 | 10/2015 | Badylak et al. | |
| 2018/0085494 A1 | 3/2018 | Fawdry et al. | |

OTHER PUBLICATIONS

Barkai, Uriel et al., "Survival of encapsulated islets: More than a membrane story," World Journal of Transplantation Mar. 24, 2016; 6(1): 69-90 (23 pages).
Dieterich, M. et al., "Biological Matrices and Synthetic Meshes Used in Implant-based Breast Reconstruction—a Review of Products Available in Germany," Geburtshilfe und Frauenheilkunde. Nov. 2013; 73(11): 1100-1106 (16 pages).
File History for U.S. Appl. No. 15/717,201 downloaded Jun. 2, 2021 (193 pages).
Jayanth, S.T. et al., "A randomized controlled experimental study comparing chitosan coated polypropylene mesh and Proceed mesh for abdominal wall defect closure," Annals of Medicine and Surgery 4 (2015) 388-394 (7 pages).
O'Sullivan, Esther S. et al., "Islets Transplanted in Immunoisolation Devices: A Review of the Progress and the Challenges that Remain," Endocrine Reviews, Dec. 2011, 32(6): 827-844 (18 pages).
Sakata, Naoaki et al., "Encapsulated islets transplantation: Past, present and future," World Journal of Gastrointestinal Pathophysiology Feb. 15, 2012; 3(1): 19-26 (8 pages).
Schweicher, Julien et al., "Membranes to Achieve Immunoprotection of Transplanted Islets," Front Biosci (Landmark Ed).; 19:49-76 (53 pages).
Shin, Y. M. et al., "Experimental Characterization of Electrospinning: The Electrically Forced Jet and Instabilities," Polymer 42 (2001) 9955-9967 (13 pages).

\* cited by examiner (Continued)

*Primary Examiner* — Robert A Wax
*Assistant Examiner* — Quanglong N Truong
(74) *Attorney, Agent, or Firm* — Pauly, DeVries Smith & Deffner LLC (57) ABSTRACT

Embodiments herein relate to cell encapsulation membranes, devices including the same, and related methods. In an embodiment, a cell encapsulation membrane is included. The cell encapsulation membrane can include a mesh substrate. The mesh substrate can include a first series of fibers extending in a first direction and a second series of fibers extending in a second direction, the first series of fibers intersecting with the second series of fibers, the mesh substrate defining a plurality of apertures disposed between adjacent fibers of the first series and the second series. The cell encapsulation membrane can further include a coating disposed on the mesh substrate, the coating partially occluding the plurality of apertures defined by the mesh substrate and forming pores. Other embodiments are also included herein.

19 Claims, 9 Drawing Sheets

CELL ENCAPSULATION MEMBRANES, DEVICES AND METHODS

This application is a divisional of U.S. application Ser. No. 15/717,201, filed Sep. 27, 2017, which claims the benefit of U.S. Provisional Application No. 62/400,754, filed Sep. 28, 2016, the contents of which are herein incorporated by reference in their entireties.

FIELD

Embodiments herein relate to cell encapsulation membranes, devices including the same, and related methods.

BACKGROUND

The implantation of living cells promises to be an effective treatment for some conditions. By way of example, it has been theorized that diabetes can be treated by implanting cells producing insulin (beta cells or other cells engineered to produce insulin) into a subject.

However, cell implantation treatments have proven to be more difficult in practice than expected. Various problems can arise. For example, the host immune system can attack implanted cells. This has led to approaches where the cells are physically separated from the host environment within a porous bag or device. However, if the transplanted cells are within a porous pouch or container, it can be challenging to ensure that enough oxygen and nutrients will reach the transplanted cells to sustain them. In addition, biofouling tends to occur on the surfaces of the implanted devices and can further reduce the ability of oxygen and nutrients to reach the transplanted cells.

SUMMARY

Embodiments herein relate to cell encapsulation membranes, devices including the same, and related methods. In an embodiment, a cell encapsulation membrane is included. The cell encapsulation membrane can include a mesh substrate. The mesh substrate can include a first series of fibers extending in a first direction and a second series of fibers extending in a second direction, the first series of fibers intersecting with the second series of fibers, the mesh substrate defining a plurality of apertures disposed between adjacent fibers of the first series and the second series. The cell encapsulation membrane can further include a coating disposed on the mesh substrate, the coating partially occluding the plurality of apertures defined by the mesh substrate and forming pores.

In addition to one or more of the preceding or following aspects, or in the alternative to some aspects, in a second aspect the plurality of apertures disposed between adjacent fibers of the first series and second series have an average width of 5 microns to 50 microns.

In addition to one or more of the preceding or following aspects, or in the alternative to some aspects, in a third aspect the pores in the coating have a different shape than the apertures defined by the mesh substrate.

In addition to one or more of the preceding or following aspects, or in the alternative to some aspects, in a fourth aspect the pores have an average opening width of 500 nm to 5 microns.

In addition to one or more of the preceding or following aspects, or in the alternative to some aspects, in a fifth aspect the pores can be webbed pores.

In addition to one or more of the preceding or following aspects, or in the alternative to some aspects, in a sixth aspect the coating can be a polymeric coating.

In addition to one or more of the preceding or following aspects, or in the alternative to some aspects, in a seventh aspect the thickness of the polymeric coating disposed over the mesh substrate varies in thickness radially around the lengthwise axis of each fiber in the first series and the second series.

In addition to one or more of the preceding or following aspects, or in the alternative to some aspects, in an eighth aspect the thickness of the polymeric coating disposed over the mesh substrate varies in thickness radially around the lengthwise axis of each fiber in the first series and the second series and is thicker on a side of each fiber that is between adjacent fibers than on sides of the fibers facing an outer or inner surface of the cell encapsulation membrane.

In addition to one or more of the preceding or following aspects, or in the alternative to some aspects, in a ninth aspect the polymeric coating is spray-coated.

In addition to one or more of the preceding or following aspects, or in the alternative to some aspects, in a tenth aspect the polymeric coating includes a polymer selected from the group consisting of SIBS, PIB-PUR, and silicone, and polycarbonate urethane.

In addition to one or more of the preceding or following aspects, or in the alternative to some aspects, in an eleventh aspect the polymeric coating comprising a partially-fused particulate polymeric coating.

In addition to one or more of the preceding or following aspects, or in the alternative to some aspects, in a twelfth aspect the pores formed by the polymeric coating are aligned with the plurality of apertures defined by the mesh substrate, the polymeric coating further comprising a second set of pores that are not aligned with the apertures defined by the mesh substrate.

In addition to one or more of the preceding or following aspects, or in the alternative to some aspects, in a thirteenth aspect the polymeric coating further comprising a second set of pores with an average size that is smaller than the pores formed by the polymeric coating partially occluding the plurality of apertures defined by the mesh substrate.

In addition to one or more of the preceding or following aspects, or in the alternative to some aspects, in a fourteenth aspect the coating comprising a metal or metal oxide coating.

In addition to one or more of the preceding or following aspects, or in the alternative to some aspects, in a fifteenth aspect the coating comprising a Ti or $TiO_2$.

In addition to one or more of the preceding or following aspects, or in the alternative to some aspects, in a sixteenth aspect, the coating comprising a first polymer coating layer and a second metal or metal oxide coating layer.

In addition to one or more of the preceding or following aspects, or in the alternative to some aspects, in a seventeenth aspect the average total thickness of the mesh substrate and the coating disposed on the mesh substrate is from 50 microns to 100 microns.

In addition to one or more of the preceding or following aspects, or in the alternative to some aspects, in an eighteenth aspect the average total thickness of the mesh substrate is from 30 microns to 40 microns.

In addition to one or more of the preceding or following aspects, or in the alternative to some aspects, in a nineteenth aspect the first series of fibers and second series of fibers comprise a polymer selected from the group consisting of polyesters, polyamides, and polyethersulfones.

In addition to one or more of the preceding or following aspects, or in the alternative to some aspects, in a twentieth aspect the first series of fibers and second series of fibers are arranged substantially perpendicularly to one another.

In addition to one or more of the preceding or following aspects, or in the alternative to some aspects, in a twenty-first aspect the first series of fibers and second series of fibers are arranged with their lengthwise axes at an angle of about 15 degrees to 90 degrees to one another.

In addition to one or more of the preceding or following aspects, or in the alternative to some aspects, in a twenty-second aspect the first series of fibers and second series of fibers are arranged in a weave pattern with respect to one another.

In addition to one or more of the preceding or following aspects, or in the alternative to some aspects, in a twenty-third aspect a hydrogel layer can be disposed over polymeric coating on one side of the cell encapsulation membrane.

In addition to one or more of the preceding or following aspects, or in the alternative to some aspects, in a twenty-fourth aspect the hydrogel layer can be a polymer selected from the group consisting of hyaluronic acid, polyethylene glycol, polylactic acid, polyglycolide, and copolymers thereof.

In addition to one or more of the preceding or following aspects, or in the alternative to some aspects, in a twenty-fifth aspect the hydrogel layer can have an angiogenic active agent disposed therein.

In addition to one or more of the preceding or following aspects, or in the alternative to some aspects, in a twenty-sixth aspect the angiogenic active agent is distributed within the hydrogel layer forming a concentration gradient with a higher concentration on the outside surface and a lower concentration on the inside surface.

In addition to one or more of the preceding or following aspects, or in the alternative to some aspects, in a twenty-seventh aspect the angiogenic active agent can be VEGF.

In addition to one or more of the preceding or following aspects, or in the alternative to some aspects, in a twenty-eighth aspect an implantable device is included, having a first cell encapsulation membrane, a second cell encapsulation membrane, and a volume disposed between the first cell encapsulation membrane and the second cell encapsulation membrane.

In addition to one or more of the preceding or following aspects, or in the alternative to some aspects, in a twenty-ninth aspect a method of making a cell encapsulation membrane is included. The method can include applying a polymeric coating onto a mesh substrate, the polymeric coating partially occluding the plurality of apertures defined by the mesh substrate and forming pores. The method can further include applying a hydrogel layer onto one side of the polymeric coating.

In addition to one or more of the preceding or following aspects, or in the alternative to some aspects, in a thirtieth aspect a cell encapsulation membrane is included. The cell encapsulation membrane can include a mesh substrate. The mesh substrate can include a first series of fibers extending in a first direction and a second series of fibers extending in a second direction. The first series of fibers can intersect with the second series of fibers. The mesh substrate can define a plurality of apertures disposed between adjacent fibers of the first series and the second series. A coating can be disposed on the mesh substrate, the coating forming a plurality of hollow domes in the apertures between adjacent fibers of the first series and the second series.

In addition to one or more of the preceding or following aspects, or in the alternative to some aspects, in a thirty-first aspect a method of making a cell encapsulation membrane is included. The method can include applying a polymeric coating onto a mesh substrate. The method can further include deforming the polymeric coating to form a plurality of hollow domes in the apertures between adjacent fibers of the first series and the second series.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

The embodiments described herein are not intended to be exhaustive or to limit the invention to the precise forms disclosed in the following detailed description. Rather, the embodiments are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As described above, the implantation of living cells has proven to be challenging. However, cell encapsulation membranes are included herein that can effectively shield the transplanted cells from the host immune system, allow for high transport and low diffusion time of dissolved gases, nutrients, and waste, and resist biofouling. It has been found that exquisite control over the porosity of a cell encapsulation membrane can be achieved by starting with a mesh substrate and then depositing a material over the mesh in such as manner so as to control the porosity, including pore number and pore size, of the resulting membrane.

Figure 1:
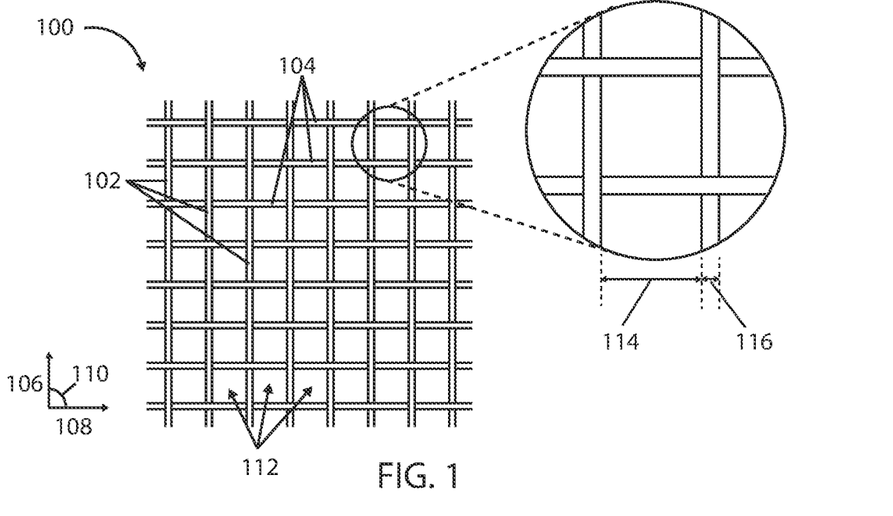
FIG. 1 is a schematic view of a mesh substrate in accordance with various embodiments herein.

Referring now to FIG. 1, a schematic view is shown of a mesh substrate 100 in accordance with various embodiments herein. The mesh substrate 100 can include a first series of fibers 102 and a second series of fibers 104. The first series of fibers 102 can extend in a first direction 106 and the second series of fibers 104 can extend in a second direction 108. The first series of fibers 102 can intersect with the second series of fibers 104. The intersection of the lengthwise axis of the first series of fibers 102 and the lengthwise axis second series of fibers 104 corresponds to angle 110.

In some embodiments, angle 110 is about 0 degrees to 90 degrees. In some embodiments, angle 110 is about 15 degrees to 90 degrees. In some embodiments, angle 110 is about 15 degrees to 165 degrees. In some embodiments, angle 110 is about 25 degrees to 155 degrees. In some embodiments, angle 110 is about 35 degrees to 145 degrees. In some embodiments, angle 110 is about 45 degrees to 135 degrees. In some embodiments, angle 110 is about 55 degrees to 125 degrees. In some embodiments, angle 110 is about 65 degrees to 115 degrees. In some embodiments, angle 110 is about 75 degrees to 105 degrees.

The mesh substrate 100 defines a plurality of apertures 112 (or gaps, spaces, pores, voids, or the like) disposed between adjacent fibers of the first series and the second series. In some embodiments, the average width 114 of apertures 112 is between 2 microns to 200 microns. In some embodiments, the average width 114 of apertures 112 is between 5 microns to 50 microns. Further details regarding the average width 114 of apertures 112 are discussed below.

The first series of fibers 102 and the second series of fibers 104 are comprised of fibers with an average fiber diameter 116. In some embodiments, the average fiber diameter 116 is between 10 to 200 microns. In some embodiments, the average fiber diameter 116 is between 25 to 100 microns. In some embodiments, the average fiber diameter 116 is between 30 to 50 microns. In some embodiments the average fiber diameter is between 50 to 75 microns.

Figure 2:
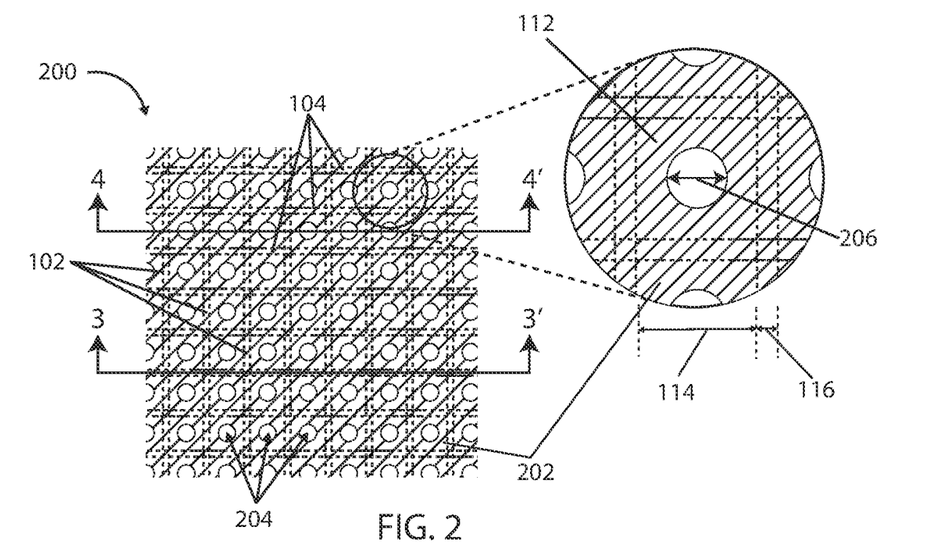
FIG. 2 is a schematic view of a cell encapsulation membrane in accordance with various embodiments herein.

Referring now to FIG. 2, a schematic view is shown of a cell encapsulation membrane 200 in accordance with various embodiments herein. The cell encapsulation membrane 200 can include a mesh substrate 100. The mesh substrate 100 of cell encapsulation membrane 200 can define a plurality of apertures 112 disposed between adjacent fibers of the first series and the second series.

The cell encapsulation membrane 200 can include a polymeric coating 202 disposed on the mesh substrate 100. The polymeric coating 202 can partially occlude the plurality of apertures 112, defined by the mesh substrate. The polymeric coating 202 can form pores 204 that can have the same shape or different shape than apertures 112. The pores 204 can have an average opening width 206 of between 250 nm to 10 microns. In some embodiments, the pores 204 can have an average opening width 206 of between 500 nm to 5 microns. Additional values for the upper and lower limits of the average opening width 206 for some embodiments are discussed below.

Figure 3:
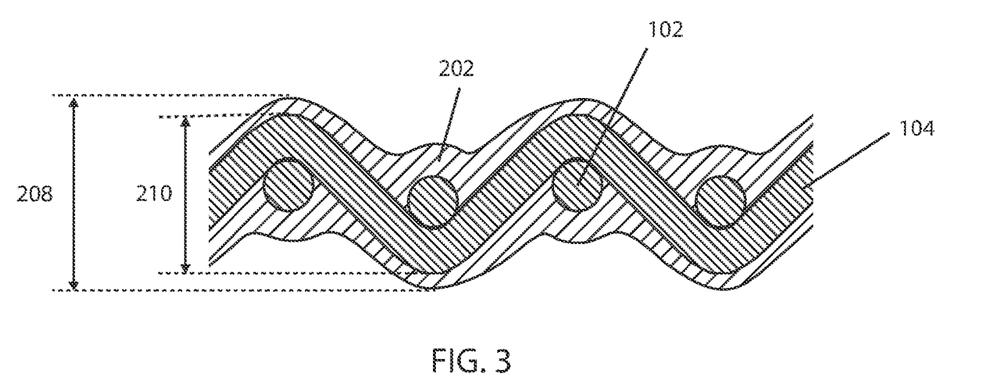
FIG. 3 is a schematic cross-sectional view of a cell encapsulation membrane as viewed along axis 3-3' of FIG. 2.

Referring now to FIG. 3, a cross-sectional view is shown of cell encapsulation membrane 200 as viewed along axis 3-3' from FIG. 2. FIG. 3 shows the first series of fibers 102 and a second series of fibers 104 having disposed thereon a polymeric coating 202. The average total thickness 208 of the mesh substrate coated with polymeric coating 202 can be between 20 to 250 microns, 25 microns to 150 microns, or 50 to 100 microns. The average total thickness 210 of the mesh substrate without a polymeric coating can be between 10 to 150 microns, or 20 to 60 microns, or 30 to 40 microns. Further details regarding the average total thickness 208 of mesh substrate with a polymeric coating and the average total thickness 210 of mesh substrate without a polymeric coating are discussed below.

Figure 4:
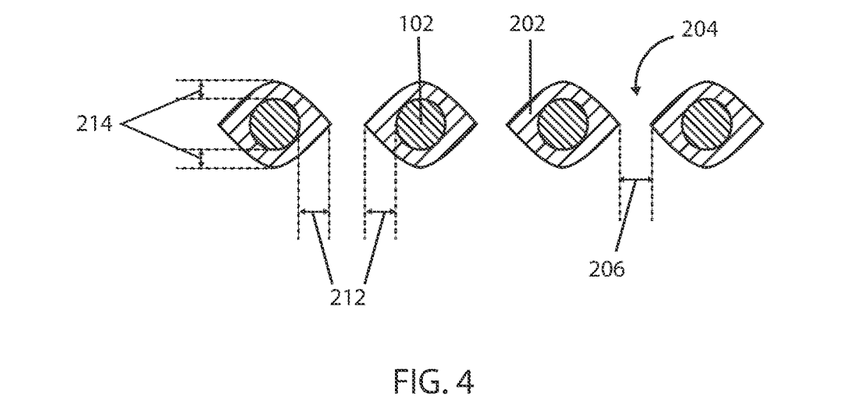
FIG. 4 is a schematic cross-sectional view of a cell encapsulation membrane as viewed along axis 4-4' of FIG. 2.

Referring now to FIG. 4, a cross-sectional view is shown of cell encapsulation membrane 200 as viewed along axis 4-4' from FIG. 2. FIG. 4 shows polymeric coating 202 disposed over the first series of fibers 102 of the mesh substrate. The pores 204 are shown disposed between adjacent fibers of the mesh substrate. Pores 204 can have an average opening width 206, as set forth herein. The polymeric coating 202 disposed over the mesh substrate can vary in thickness radially around the lengthwise axis of each fiber in the first series and the lengthwise axis of each fiber in the second series. In some embodiments, polymeric coating 202 is thicker on a side 212 of each fiber that is between adjacent fibers than on a side 214 of each fiber facing an outer or inner surface of the cell encapsulation membrane 200.

Figure 5:
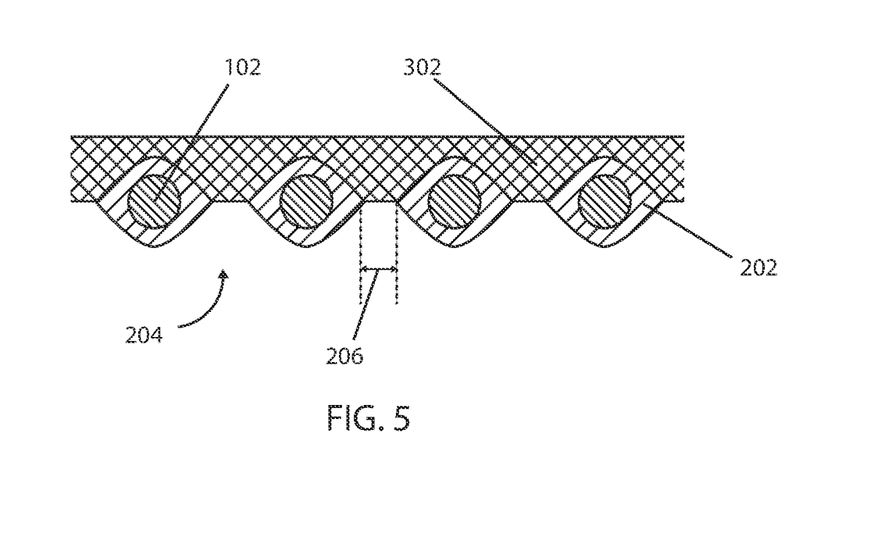
FIG. 5 is a schematic cross-sectional view of a cell encapsulation membrane including a hydrogel layer in accordance with various embodiments herein.

In some embodiments, the cell encapsulation membrane can also include a hydrogel layer. In some embodiments, the hydrogel layer can include an agent to promote vascularization of the cell encapsulation membrane. Referring now to FIG. 5, a schematic view is shown of a hydrogel layer disposed on cell encapsulation membrane in accordance with various embodiments herein. Hydrogel layer 302 can be disposed over polymeric coating 202 on one side of the cell encapsulation membrane 300. In other embodiments, the hydrogel layer can be disposed over both sides of the cell encapsulation membrane. Pores 204 are shown disposed between adjacent fibers of the mesh substrate. Pores 204 have an average opening width 206, as set forth herein.

Mesh Substrates

Figure 6:
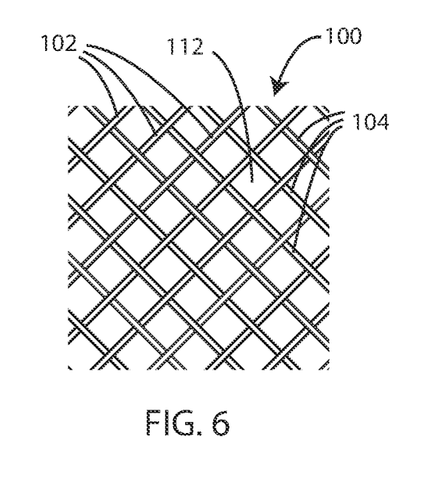
FIG. 6 is a schematic view of a mesh substrate in accordance with various embodiments herein.
Figure 7:
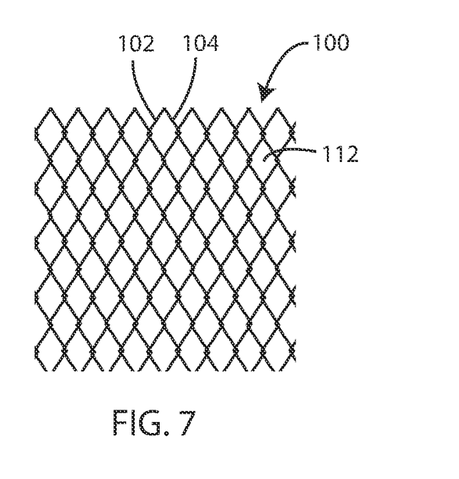
FIG. 7 is a schematic view of a mesh substrate in accordance with various embodiments herein.

It will be appreciated that mesh substrates used herein can have various patterns of fibers. By way of example, while FIG. 1 shows series of fibers intersecting each other in a standard grid arrangement, the fibers can also form other patterns. By way of example, referring to FIG. 6, a mesh substrate in accordance with various embodiments herein is shown. In FIG. 6, the mesh substrate 100 includes a first series of fibers 102 and a second series of fibers 104. Disposed between adjacent fibers are a plurality of apertures 112. In this case, the fibers intersect one another in a manner so as to result in apertures having diamond shapes. Further, referring to FIG. 7, a schematic view of a mesh substrate in accordance with various embodiments herein is shown. In FIG. 7, the mesh substrate 100 includes a first series of fibers 102 and a second series of fibers 104. In this example the fibers are arranged in a pattern similar to a chain link fence wherein the first series of fibers 102 and second series of fibers 104 have an overall lengthwise direction that is substantially parallel to one another, but individual segments of each fiber are angled such that the fibers intersect forming a pattern defining apertures 112. In some examples, the fibers intersect and overlap. In other examples the fibers intersect but only make contact without overlapping. It will be appreciated that many different types of patterns of fiber arrangement are possible and are contemplated herein. Other patterns can include variations on weave patterns, honeycomb patterns, dot patterns, knit patterns and the like.

It will be appreciated that the mesh substrates described herein can be formed from many types of fibers. Fibers can include polymeric fibers, metal fibers, glass fibers, composite fibers, and the like. In some embodiments, the fibers are formed from a thermoplastic polymer. In other embodiments, the fibers are formed from a thermoset polymer. In some embodiments, fiber types used to create the mesh substrates can include those comprised of biologically stable polymers such as polyester, polyimide, polyamide, polyethersulfone, polyethylene, polypropylene, polytetrafluoroethylene, ethylene-co-vinyl acetate, polydimethylsiloxane, poly(ether-urethane), polyethylene terephthalate, polymethylmethacrylate, polysulfone, polyethylene oxide, polycarbonate, poly(vinylidene fluoride-co-hexafluoropropylene) (PVDF-HFP), and any similar polymer or a combination thereof. In some embodiments, the material for the fibers is selected from the group consisting of a polyester, a polyamide, and a polyethersulfone. It will be appreciated that methods for increasing the hydrophilicity of polymers can be used in accordance with the embodiments herein. By way of example, increasing the hydrophilicity of polymers can be accomplished through the method of pegylation, the process of attaching polyethylene glycol (PEG) polymer chains to various molecules or macrostructures, such as the polymeric fibers described herein.

In various embodiments, the fiber types used in the mesh substrates embodied herein are biologically compatible such that they do not produce a negative response when present within living tissue. In some embodiments, the fiber types used to create mesh substrates can be biologically absorbable.

Fibers can be comprised of a monofilament, a multifilament, a braided multifilament, or the like.

In some embodiments of the mesh substrates described herein, a first series of fibers and a second series of fibers can be arranged such that a plurality of apertures are disposed between adjacent fibers of the first series and the second series. The size of the apertures within the mesh substrates described herein can be highly controlled by the specific arrangement of the first series of fibers and the second series of fibers. In some embodiments, the lower limit of the average width of the apertures is 500 nm, 1 micron, 2 microns, 3 microns, 4 microns, 5 microns, 10 microns, 15 microns, 20 microns, 25 microns, 30 microns, 40 microns, or 50 microns. In some embodiments, the upper limit of the average width of the pores is 10 microns, 20 microns, 30 microns, 40 microns, 50 microns, 60 microns, 70 microns, 80 microns, 90 microns, 100 microns, 200 microns, 300 microns, 400 microns, or 500 microns.

The mesh substrates described herein may be formed of fibers arranged in various patterns. In some embodiments, the first series of fibers and second series of fibers are arranged in a weave pattern with respect to one another. In some embodiments, the first series of fibers and second series of fibers are arranged in plain weave pattern, a twill weave pattern, a basket weave pattern, a honeycomb pattern, a grid pattern, a satin weave pattern, webbed pattern, or any other suitable pattern. In some embodiments, the first series of fibers and second series of fibers are arranged substantially perpendicularly to one another.

In some embodiments, the mesh substrates could be formed from a random array of polymeric fibers created using an electrospinning process. In some embodiments, an electrospun layer of fibers could be deposited on the mesh substrate to create a mesh substrate-electrospun layer hybrid. Electrospinning (or electrostatic fiber formation or electrospraying) is a fiber production method which uses electric force to draw charged threads of polymer solutions or polymer melts. When a sufficiently high voltage is applied to a liquid droplet, the body of the liquid becomes charged, and electrostatic repulsion counteracts the surface tension and the droplet is stretched. At a critical point, a stream of liquid erupts from the surface. This point of eruption is known as the Taylor cone. If the molecular cohesion of the liquid is sufficiently high, stream breakup does not occur and a charged liquid jet is formed. As the jet dries in flight, the mode of current flow changes from ohmic to convective as the charge migrates to the surface of the fiber. The jet is then elongated by a whipping process caused by electrostatic repulsion initiated at small bends in the fiber, until it is finally deposited on the grounded collector. The elongation and thinning of the fiber resulting from this bending instability leads to the formation of substantially uniform fibers with nanometer-scale diameters. Electrospinning methods are described in Shin, Hohman, Brenner, and Rutledge, "Experimental Characterization of electrospinning: the electrically forced jet and instabilities", Polymer 42, 9955-9967, (2001), incorporated herein by reference in its entirety. A particular type of electrospinning, known as flow-limited field-injection electrostatic spraying (FFESS), is described in U.S. Patent Application Publication No. 2004/0022939, the content of which is herein incorporated by reference.

In some embodiments, the patterns used to create the mesh substrates described herein can be formed by braiding, weaving, interweaving, knitting, or non-woven methods. By way of example, non-woven fiber arrangements can include a fiber mat arrangement. In some embodiments, the mesh substrate can be made from a solid polymeric sheet. In some embodiments, the mesh substrate can be made from a dense weave of polymer fibers having little to no spacing between fibers. In some embodiments, holes of any of a number of geometric shapes can be punched or cut into a solid polymeric sheet, a fiber mat, or a dense weave fabric.

In some embodiments, cell encapsulation membranes or portions thereof such as mesh substrates can be compressed. By way of example, cell encapsulation membranes or layers can be compressed together through the application of heat and/or pressure. In some embodiments, the compression can reduce the thickness of the cell encapsulation membrane or a portion thereof. In some embodiments, the compression can reduce the size of apertures disposed between fibers and/or reduce the size of other pores in the cell encapsulation membrane.

In some embodiments, the mesh substrates described herein may be comprised of fibers oriented in a uniform pattern having a uniform distribution of aperture size. In some embodiments, the mesh substrates described herein may be comprised of fibers oriented in a non-uniform pattern having a non-uniform aperture size distribution. In some embodiments, the lower limit of the average total thickness of the mesh substrate is 5 microns, 10 microns, 20 microns, 30 microns, 40 microns, or 50 microns. In some embodiments, the upper limit of the average total thickness of the mesh substrate is 10 microns, 20 microns, 30 microns, 40 microns, 50 microns, 60 microns, 70 microns, 80 microns, 90 microns, 100 microns, 150 microns, or 200 microns.

In some embodiments, the apertures between adjacent fibers are substantially polygonal, being framed by the surrounding fibers of the mesh. For example, the apertures can be square, rectangular, etc. In some embodiments, the apertures are non-polygonal. In some embodiments, the apertures can be irregular.

Polymeric Mesh Coatings

In various embodiments, the mesh substrates described herein can be coated with a polymeric coating. Polymer coated mesh substrates can form a cell encapsulation membrane. Suitable polymers can include those than can be spray coated. However, non-spray coated polymers can also be included herein. In some embodiments, polymers used to form the coating can include those that are substantially non-degradable under normal physiological conditions. Polymers used to form the coating can include hydrophilic polymers. However, in some embodiments, non-hydrophilic polymers can also be used. Suitable polymers used to coat a mesh substrate can specifically include, but are not limited to, styrene isoprene butadiene (SIBS), polyisobutylene polyurethane (PIBPUR), silicone, solution-based polycarbonate urethanes such as CHRONOFLEX® (commercially available from AdvanSource Biomaterials, Wilmington, Mass.), or any similar polymer or combination thereof. Other polymers that can be used to coat a mesh substrate can include polyurethanes, polyurea, polyether ether ketone (PEEK), polyamides, styrene butadiene rubber (SBR), polyethylene, polyethylene-co-vinyl acetate, polycarbonate, polymethylmethacrylate (PMMA), and copolymers including any of these.

Polymeric coatings can be precisely deposited on the mesh substrate using various techniques to create finely controlled pores of desired size nestled within the individual pores of the underlying mesh substrate. In some embodiments, particularly where a polymeric coating is applied via a spray, the pores can form webbed pores. While not intending to be bound by theory, it is believed that surface tension effects can impact the shape of the pore that is formed particularly when the polymer is deposited from a spray.

In some embodiments, the lower limit of the average opening width of the pores is 50 nm, 100 nm, 200 nm, 300 nm, 400 nm, 500 nm, 600 nm, 700 nm, 800 nm, 900 nm, or 1 micron. In some embodiments, the upper limit of the average opening width of the pores is 500 nm, 1 micron, 2 microns, 3 microns, 4 microns, 5 microns, 10 microns, 15 microns, 20 microns, or 25 microns.

In some embodiments, the lower limit of the average total thickness of the mesh substrate coated with polymeric coating is 5 microns, 10 microns, 20 microns, 30 microns, 40 microns, or 50 microns. In some embodiments, the upper limit of the average total thickness of the mesh substrate coated with polymeric coating is 20 microns, 30 microns, 40 microns, 50 microns, 60 microns, 70 microns, 80 microns, 90 microns, 100 microns, 150 microns, or 200 microns.

It will be appreciated that, beyond the pores formed that align with apertures in the mesh substrate, that the polymer used to create the coating may itself be porous. For example, the polymer may be applied (with or without a solvent) in a manner so as to create a porous polymeric matrix. In this case, the polymeric layer may include a second set of pores that are not aligned with the apertures defined by the mesh substrate. The second set of pores can have an average size that is smaller than the pores formed by the polymeric coating partially occluding the plurality of apertures defined by the mesh substrate. As such, in various embodiments the first and second sets of pores can be different from one another in terms of position, average size, number, shape, etc. In some embodiments, the second set of pores are more irregular than the pores that are aligned with the apertures defined by the mesh substrate.

Figure 8:
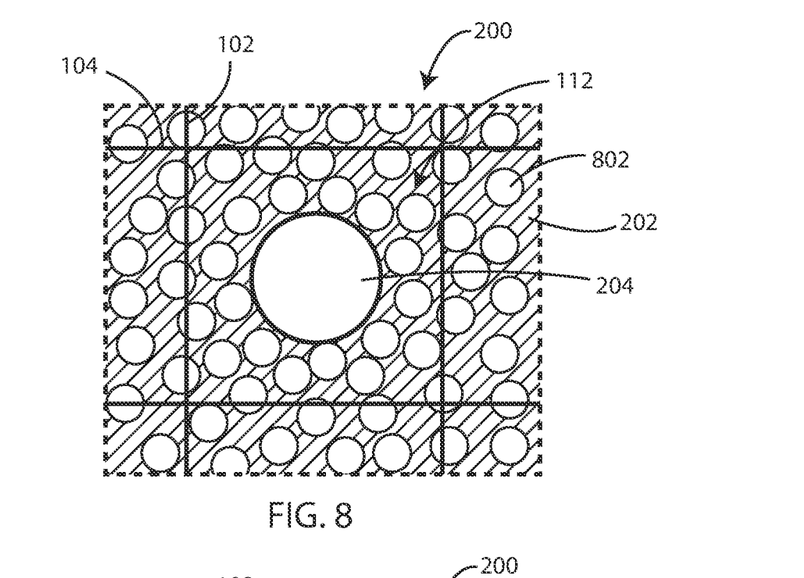
FIG. 8 is a schematic view of a cell encapsulation membrane in accordance with various embodiments herein.

Referring now to FIG. 8, a schematic view is shown of a cell encapsulation membrane 200 in accordance with various embodiments herein. The cell encapsulation membrane 200 can include a mesh substrate formed with fibers 102 and 104. The mesh substrate fibers define a plurality of apertures 112 disposed between adjacent fibers of the mesh substrate.

The cell encapsulation membrane 200 can include a polymeric coating 202 disposed on the mesh substrate. The polymeric coating 202 can partially occlude the plurality of apertures 112, defined by the mesh substrate. The polymeric coating 202 can form pores 204 (or aligned pores) that can have the same shape or different shape than apertures 112. The polymeric coating 202 can also include pores 802 (or non-aligned pores) that are not aligned with the apertures 112. In some embodiments, the non-aligned pores 802 can be interconnected. The non-aligned pores 802 can be, on average, smaller than the aligned pores 204. However, in other embodiments, the non-aligned pores 802 can be the same size as the aligned pores 204. The polymeric layer can be made to include the non-aligned pores in various ways. By way of example, in the context of some polymers, the inclusion of an amount of water with the polymer solvent can result in the formation of a porous polymer. Many other techniques of making a polymer porous can be used.

In various embodiments, pores herein (whether aligned or non-aligned pores) can pass directly through the cell encapsulation membrane or portions thereof in a relatively straight line. However, in some embodiments, pores herein may not pass through in a straight line. In some cases, the pore may follow a curved or circuitous path through the cell encapsulation membrane.

Figure 9:
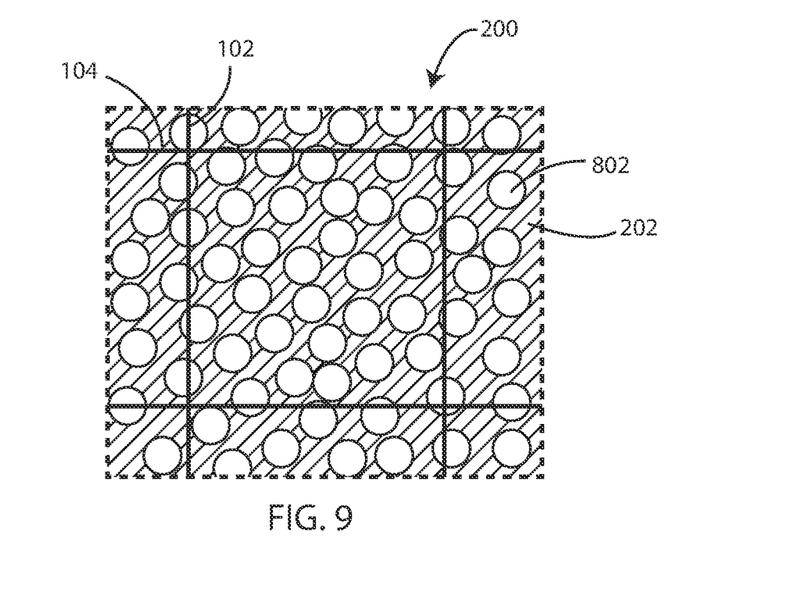
FIG. 9 is a schematic view of a cell encapsulation membrane in accordance with various embodiments herein.

In some embodiments, aligned pores can be omitted from the cell encapsulation membrane. Referring now to FIG. 9, a schematic view is shown of a cell encapsulation membrane 200 in accordance with various embodiments herein. The cell encapsulation membrane 200 can include a mesh substrate formed with fibers 102 and 104. The mesh substrate fibers define a plurality of apertures 112 disposed between adjacent fibers of the mesh substrate. The cell encapsulation membrane 200 can include a polymeric coating 202 disposed on the mesh substrate. The polymeric coating 202 can occlude the plurality of apertures 112, defined by the mesh substrate. The polymeric coating 202 can include pores 802 (or non-aligned pores) that are not aligned with the apertures 112.

Figure 10:
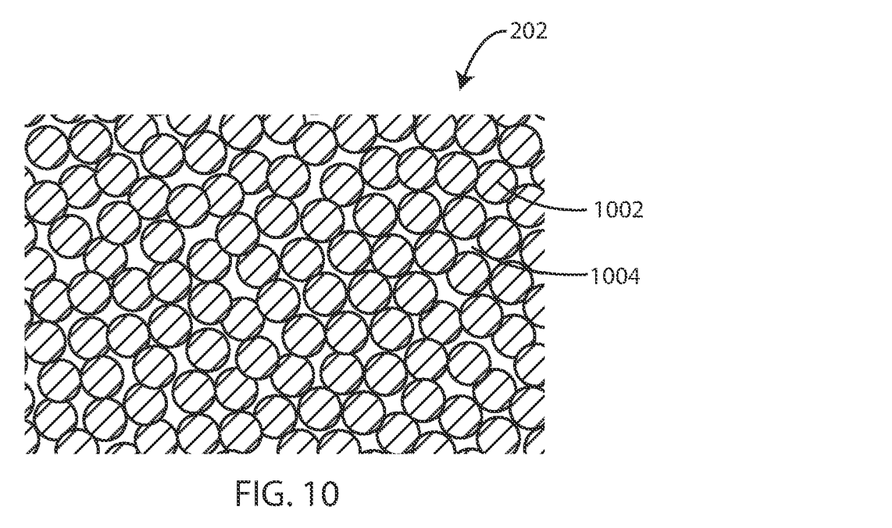
FIG. 10 is a porous polymer layer formed with a partially fused particulate polymer in accordance with various embodiments herein.

Polymeric coatings can be deposited on the mesh substrate in a manner so as to result in fused or at least partially fused particles with pores disposed between particles. Referring now to FIG. 10, a schematic view is shown of a polymer coating 202 (or layer) formed with a partially fused particulate polymer in accordance with various embodiments herein. The polymer coating 202 (or layer) includes a plurality of particles 1002. The particles 1002 can be fused, partially-fused, or adhered together. Pores 1004 can be disposed in between the particles 1002.

Such a particulate structure can be formed in various ways. In some embodiments, the type and/or amount of solvent used with a spray of a polymer, and in some cases the spraying conditions (spray distance, flow rate, assist gas flow rate, nozzle design, temperature, etc.), can be manipulated to result in relatively rapid flashing off of the solvent allowing only a brief amount of time for the edges of particulates to bond or fuse together, but without the opportunity for particulates to fully coalesce together. In some embodiments, a solvent with a relatively low flash-point, such as THF and/or acetone can be used. In other embodiments, a first spray deposition step can be followed by a later fusion step that can involve the application of heat to allow particles made of a thermoplastic to fuse (fully or partially) together. In some embodiments, a later step including spraying of a solvent can be used to fuse the particles together. The particular solvent can be selected based on factors such as the solubility of the polymers being used.

Methods of Applying Polymeric Coatings

Many methods for applying a polymeric coating to a mesh substrate can be used. In some embodiments, the method of applying a polymeric coating to a mesh substrate can include a spray coating process. A spray coating process can involve applying a polymeric coating to the surface of a mesh substrate using a polymer solution feed and gas assist feed coupled to a spray nozzle. Process parameters can be adjusted accordingly to provide optimal conditions for polymeric coating deposition. Properties including, but not limited to polymer molecular weight, solvent flash-point, relative humidity, water content, spray distance, polymer flow rate and assist gas flow rate can all be optimized to deposit polymeric coatings in accordance with the embodiments herein.

The optimization of process parameters can be used to precisely control the thickness of the polymeric coating and the average width of the webbed pores. The use of low flash-point solvents like tetrahydrofuran (THF), acetone, or other like solvents, coupled with optimized spray distance and flow rate can yield polymeric coatings on mesh substrates having the properties as described herein. Other parameters such nozzle design can be modified to yield polymeric coatings with pores or webbed pores as described herein.

In some embodiments, spray coating parameters can be adjusted such that the polymeric coating is deposited to form a smooth surface on mesh substrates. Cell encapsulation membranes having smooth surfaces can provide the membrane with properties desirable for minimizing tissue reaction or the development of a fibrotic capsule around the membrane when implanted into a body.

In some embodiments, spray coating parameters can be adjusted to cause a particulate deposition pattern on the surface of the mesh substrate, where the neighboring particles fuse to form webbed pores in the polymeric coating layer. In some embodiments, the water content of the polymeric coating mixture can be raised or lowered to increase or decrease the size of webbed pores within the polymeric coating layer.

Polymeric coatings can be applied to a mesh substrate using a plasma vapor deposition process. Plasma vapor deposition (PVD) techniques can be used to deposit a thin polymeric coating onto a mesh substrate in accordance with the embodiments herein. In a plasma vapor deposition process, a gas vapor phase can be converted into a thin solid film on the surface of a mesh substrate A plasma vapor deposition process for use with embodiments herein can include depositing polymeric coatings onto the mesh substrate using a plasma. PVD is a particularly useful process for fine-tuning the size of the webbed pores in accordance with the embodiments herein. In some embodiments, chemical vapor deposition (CVD) and variants thereof can also be used for the deposition process. In some embodiments, a polymeric coating can be applied by plasma polymerization.

In some embodiments, the method of applying an inorganic oxide, coating to a mesh substrate can include an atomic layer deposition (ALD) process. In accordance with the embodiments herein, the ALD process can involve depositing a conformal coating of an inorganic oxide from its gaseous phase onto the surface of a mesh substrate that has a polymeric coating. In some embodiments, the inorganic oxide can be applied directly to the mesh substrate before adding a polymeric coating to the mesh substrate. Using the ALD method, a second layer can be deposited onto the first layer in accordance with some embodiments herein. In some embodiments, the second layer can be formed from a metal or a metal oxide. An exemplary inorganic oxide in the form of a metal oxide is titanium dioxide ($TiO_2$). Alternating layers of polymeric compound and $TiO_2$ can be deposited until the desired number of layers or thickness is achieved.

Figure 11:
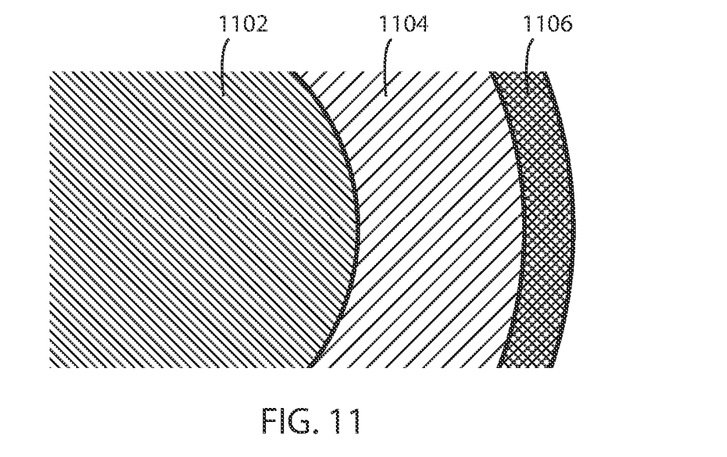
FIG. 11 is a partial cross-sectional view of a mesh fiber with a first layer and a second layer disposed thereon.

In some embodiments, the cell encapsulation membrane can include a first polymer coating layer and a second metal or metal oxide coating layer. Referring now to FIG. 11, a partial cross-sectional view of a fiber (such as from a mesh substrate) with a first layer and a second layer disposed thereon is shown. In specific, a first layer 1104 can be disposed on the fiber 1102. The first layer 1104 can be formed of various materials. However, in some embodiments, the first layer 1104 can formed of a polymeric material such as those described above. The second layer 1106 can be formed of a metal or a metal oxide, such as those described above. In various embodiments, additional layers, beyond the two shown in FIG. 11, can be included.

In various embodiments, methods of making a cell encapsulation membrane are included herein. A method of making a cell encapsulation membrane can include applying a polymeric coating onto a mesh substrate. The mesh substrate can include a first series of fibers extending in a first direction and a second series of fibers extending in a second direction. The first series of fibers can intersect with the second series of fibers. The mesh substrates used in accordance with the methods herein can define a plurality of pores disposed between adjacent fibers of the first series and the second series. The polymeric coating used in accordance with the methods herein can partially occlude the plurality of pores defined by the mesh substrate to form pores. In some methods, a hydrogel layer can be applied onto one side of the polymeric coating.

Hydrogel Layer/Angiogenic Active Agents

The cell encapsulation membranes described herein can be coated with a hydrogel layer on one side of the membrane. Suitable hydrogel compositions can be comprised of one or more of hyaluronic acid, polyethylene glycol (PEG), or other similar hydrogels or copolymers thereof. Hydrogels suitable for the embodiments herein can have a cross-linked polymeric network allowing them to hold large amounts of water. In some embodiments, bioabsorbable polymers such as polylactic acid (PLA), polylactic co-polyglycolic acid (PLGA), or other similar bioabsorbable polymers or copolymers thereof can be used in the hydrogel compositions herein. In some embodiments, the hydrogel layer can be absorbed by the body leaving behind a highly vascularized cell encapsulation membrane. In some embodiments, the hydrogel layer can be impregnated with stem cells that are pro-angiogenic, producing any number of molecules, elements, and compounds found in the angiogenic secretome In some embodiments, the hydrogel layer can be impregnated with an angiogenic active agent in order to promote vascularization of the cell encapsulation membrane. Vascularization of the cell encapsulation membrane is essential to facilitate the exchange of gases, nutrients, and waste products from encapsulated cells, tissues, or organs. Suitable angiogenic active agents can include vascular endothelial growth factor (VEGF), epidermal growth factor (EGF), fibroblast growth factor (FGF), platelet-derived growth factor (PDGF), angiogenin, or any other angiogenic active agent or combination thereof. In some embodiments, the angiogenic active agent is distributed within the hydrogel layer forming a concentration gradient with a higher concentration on the outside surface and a lower concentration on the inside surface.

In some embodiments, the hydrogel layer can be impregnated with oxygen carriers or oxygen generating systems. It is essential that encapsulated cells, tissue, and organs have access to sufficient oxygen and nutrients during the angiogenesis process. Until a competent vasculature is formed, oxygen carriers or oxygen generating systems can provide a vital source of oxygen to the cells, tissue, or organs. Suitable oxygen generating systems can include, but are not limited to, calcium peroxide-based systems. Oxygen carriers can include, but are not limited to, microparticles or micelles containing a perfluorocarbon such as, but not limited to, perfluorodecalin. It will be appreciated that the hydrogel layer can also be impregnated with various drugs for delivery to the implant site or transplant site.

Devices

The cell encapsulation membrane created from polymer coated mesh substrates described herein can be used in various applications. In some embodiments, the cell encapsulation membrane can be used to encapsulate live cells for transplant, including but not limited to any of the following cell types: islets of Langerhans, bone marrow mononuclear cells, mesenchymal stem cells, mobilized peripheral blood mononuclear cells, endothelial progenitor cells, follicular cells, Leydig cells, ovarian cells, neural stem cells, human embryonic stem cells, pluripotent stem cells, skeletal myoblasts, cardiomyoblasts, etc. In some embodiments, the cell encapsulation membrane can be used to encapsulate a porous container of live cells. In some embodiments, the cell encapsulation membrane can be used to encapsulate living tissue. In some embodiments, the cell encapsulation membrane can be used to encapsulate living organs. In some embodiments, the cell encapsulation membrane can be used to encapsulate connective tissue scaffolds. In some embodiments, the cell encapsulation membrane can be used to encapsulate bacterial transplants such as fecal bacterial transplants.

In various embodiments, an implantable device can include a first cell encapsulation membrane and a second cell encapsulation membrane. A volume of a predetermined size can be disposed between the first cell encapsulation membrane and the second cell encapsulation membrane of the implantable device. In some embodiments, the implantable device can be comprised of a first and second cell encapsulation membrane having a volume disposed there between. The shape of the implantable device can be a pouch, a bag, an envelope, a cube, a sphere, or any other suitable 3-dimensional form. However, many different constructions are contemplated herein.

Figure 12:
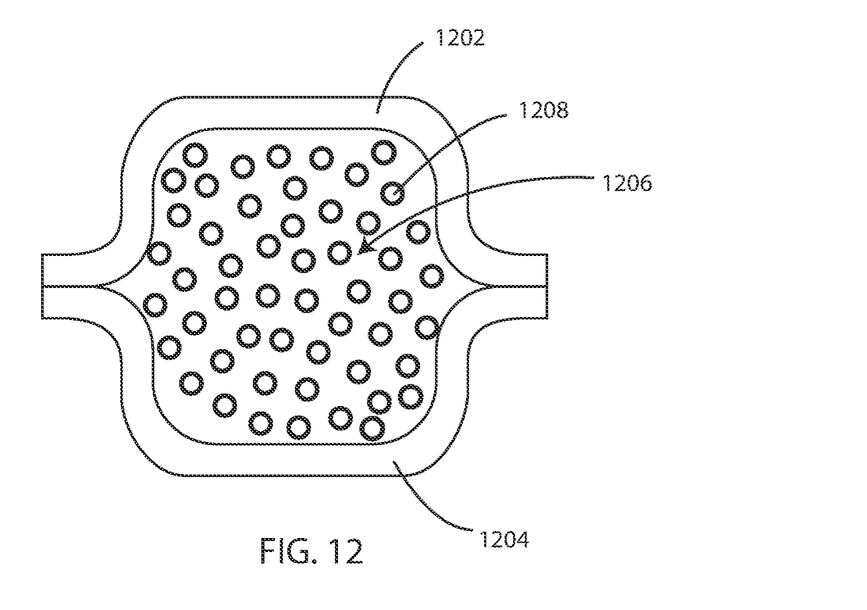
FIG. 12 is a schematic view of a device in accordance with various embodiments herein.

Referring now to FIG. 12, a device in accordance with various embodiments herein is shown. The device can include a first cell encapsulation membrane 1202, a second cell encapsulation membrane 1204, and a volume 1206 disposed between the first cell encapsulation membrane 1202 and the second cell encapsulation membrane 1204. Cells 1208 can dispose within the volume 1206.

In some embodiments, the cell encapsulation membrane can be used to form an implantable device for use in an animal. In some embodiments, the cell encapsulation membrane can be used to form an implantable device for use in a human being. In some embodiments, the cell encapsulation membrane can be used to form an implantable device for use as a delivery device. In some embodiments, the implantable device is designed for use at a site that is rich in blood supply, such as the greater momentum or interior abdominal wall. In some embodiments, the implantable device is located at a site where delivery of the contents of the implantable device is desired, such as the colon.

Further Embodiments

In some embodiments, a polymeric layer that is disposed over a mesh substrate can be further processed in order to create a cell encapsulation membrane. By way of example, in some embodiments, a polymeric coating or layer can be disposed over a mesh substrate and processed in order to form hollow domes or dome-like structures that are positioned in alignment with apertures between the fibers of the mesh substrate. The domes can increase the surface area of the cell encapsulation membrane allowing for higher transfer rates of materials such as dissolved gases across the cell encapsulation membrane. In some embodiments, the domes have an average width of 100-200 microns. In some embodiments, domes having an average width of 100-200 microns provide a hollow 3-dimensional space for infiltration of islet cells to the surface of the cell encapsulation membrane to facilitate exchange of nutrients, gases, and waste to the cell encapsulation membrane exterior. In some embodiments, wherein hollow domes are included, the mesh substrate can have apertures (or gaps between adjacent fibers) of approximately 100 to 200 microns, or 125 to 175 microns, or 140 to 160 microns, or approximately 150 microns on average. While not intending to be bound by theory, it is believed that the average diameter of islet cells is about 150 microns and so forming hollow domes using a mesh substrate with apertures of a similar size leads to hollow domes into which islet cells can be at least partially disposed leading to an enhanced ability of the islet cells to receive dissolved gases, nutrients, and the like.

Figure 13:
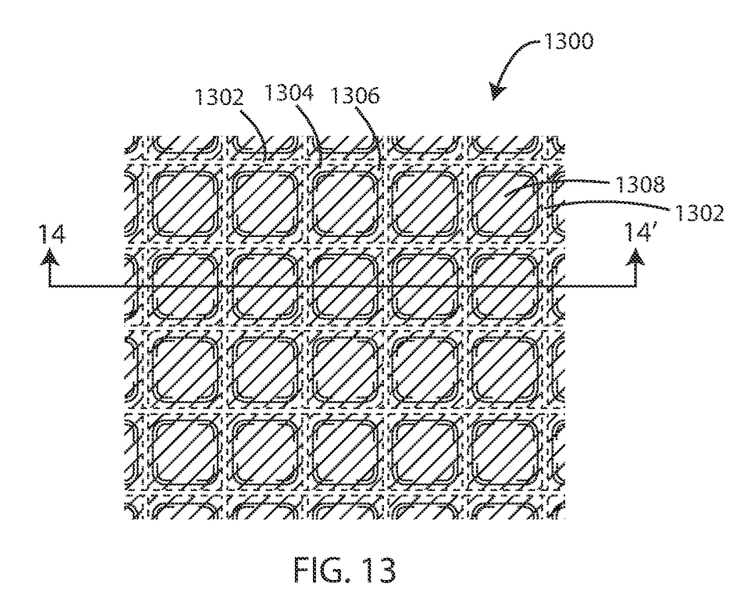
FIG. 13 is a schematic view of a cell encapsulation membrane in accordance with various embodiments herein.

Referring now to FIG. 13, a cell encapsulation membrane is shown in accordance with various embodiments herein. The cell encapsulation membrane 1300 can include a mesh substrate 1302. The mesh substrate 1302 of cell encapsulation membrane 1300 can define a plurality of apertures 1304 disposed between adjacent fibers of the mesh substrate 1302.

The cell encapsulation membrane 1300 can include a polymeric coating 1306 disposed on the mesh substrate 1302. The polymeric coating 1306 can partially occlude or fully occlude the plurality of apertures 1304, defined by the mesh substrate. The polymeric coating 1306 can include a plurality of hollow domes 1308 or dome-like structures.

Figure 14:
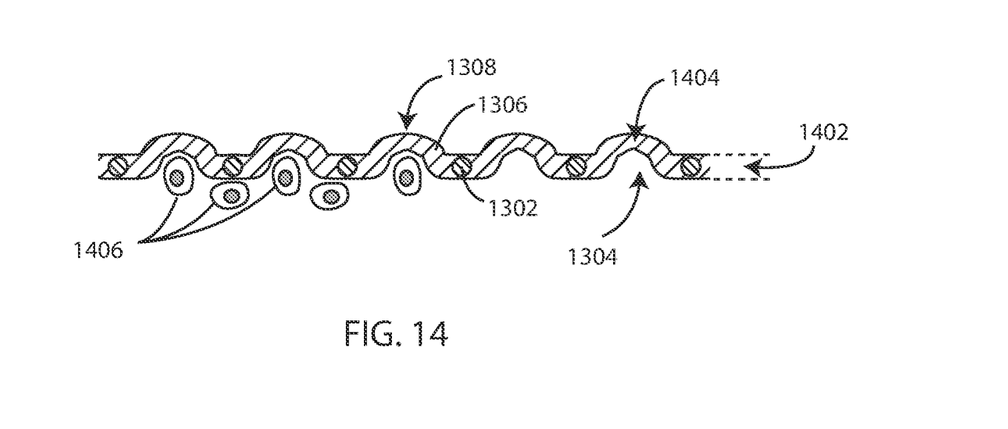
FIG. 14 is a schematic cross-sectional view of a cell encapsulation membrane as viewed along axis 14-14' of FIG. 13.

Referring now to FIG. 14, a schematic cross-sectional view of the cell encapsulation membrane of FIG. 13 is shown, as viewed along axis 14-14' of FIG. 13. The polymeric coating 1306 forms a plurality of hollow domes 1308 (or dome structures) in the apertures 1304 between adjacent fibers of the mesh substrate 1302. In this manner, the surface area of the polymeric coating 1306 (and therefore the cell encapsulation membrane) is much higher than what it would otherwise be without the hollow domes 1308. Also, in some embodiments, the thickness 1404 of the polymeric material in the hollow domes 1308 is less than the thickness 1402 of the cell encapsulation membrane in areas around the fibers of the mesh substrate 1302. This thinning of material can also enhance the transfer rates of materials such as dissolved gases across the cell encapsulation membrane In some embodiments, the hollow domes 1308 within the apertures 1304 can have an average width sufficient to allow individual islet cells 1406 to infiltrate the hollow domes 1308. The proximity of each individual islet cell 1406 to vascularization on the other side of cell encapsulation membrane can provide optimized diffusion of gasses, nutrients, and waste across the cell encapsulation membrane.

In some embodiments, fibers used herein may be circular in cross-section but in other embodiments the fibers may have a cross-sectional shape that is not circular. By way of example, in some embodiments, fibers can take on an ovoid, elliptical, irregular or non-circular shape in cross-section. In such cases, the cross-sectional dimensions can include a major axis and a minor axis. In some embodiments, the major axis of the fibers can be oriented so as to increase the overall thickness of the mesh substrate. In other embodiments, the major axis of the fibers can be oriented so as to decrease the overall thickness of the mesh substrate. In some embodiments, the major axis of fibers running in a particular direction can be oriented one way and the major axis of fibers running in a different direction can be oriented a different way. Many different configurations are contemplated herein.

Referring now to FIGS. 15-18, additional cross-sectional views are shown of embodiments of mesh substrates as viewed along axis 3-3' from FIG. 2 in accordance with some embodiments herein. In FIGS. 15-18, embodiments shown are comprised of fibers having a compressed geometry relative to those fibers shown in FIGS. 3-4. In some embodiments, the fibers may be initially formed with such a geometry. In other embodiments, the fibers may be initially formed with a substantially circular geometry and then processed to have a non-circular shape. For example, in some embodiments, the ovoid shape of the first series of fibers 102 and the second series of fibers 104 can be created by compression of fibers having a circular geometry as shown in FIGS. 3-4.

Figure 15:
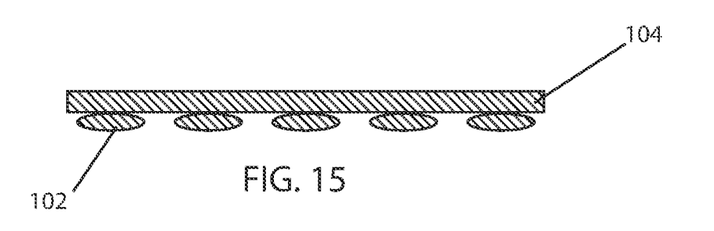
FIG. 15 is a cross-sectional view of a mesh substrate in accordance with various embodiments herein.
Figure 16:
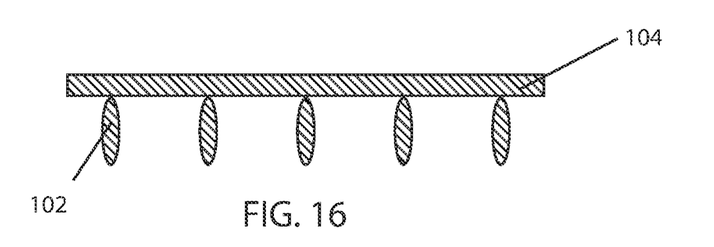
FIG. 16 is a cross-sectional view of a mesh substrate in accordance with various embodiments herein.
Figure 17:
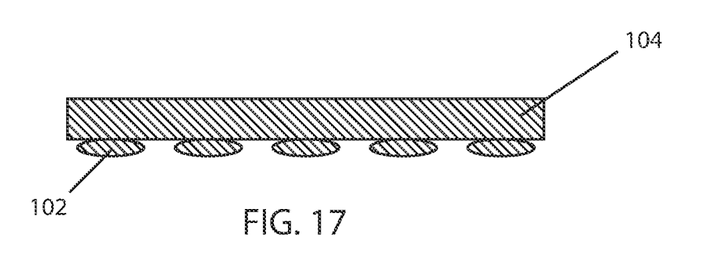
FIG. 17 is a cross-sectional view of a mesh substrate in accordance with various embodiments herein.
Figure 18:
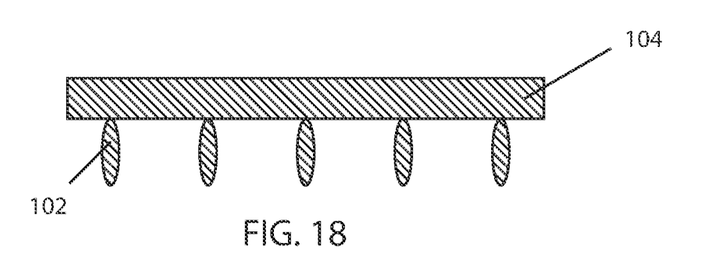
FIG. 18 is a cross-sectional view of a mesh substrate in accordance with various embodiments herein.

FIG. 15 shows the first series of fibers 102 and the second series of fibers 104 oriented with the short axis (or minor axis) of the first series of fibers 102 fused against the short axis of the second series of fibers 104. FIG. 16 shows the first series of fibers 102 and the second series of fibers 104 oriented with the long axis (or major axis) of the first series of fibers 102 fused against the short axis of the second series of fibers 104. FIG. 17 shows the first series of fibers 102 and the second series of fibers 104 oriented with the short axis of the first series of fibers 102 fused against the long axis of the second series of fibers 104. FIG. 18 shows the first series of fibers 102 and the second series of fibers 104 oriented with the long axis of the first series of fibers 102 fused against the long axis of the second series of fibers 104.

Figure 19:
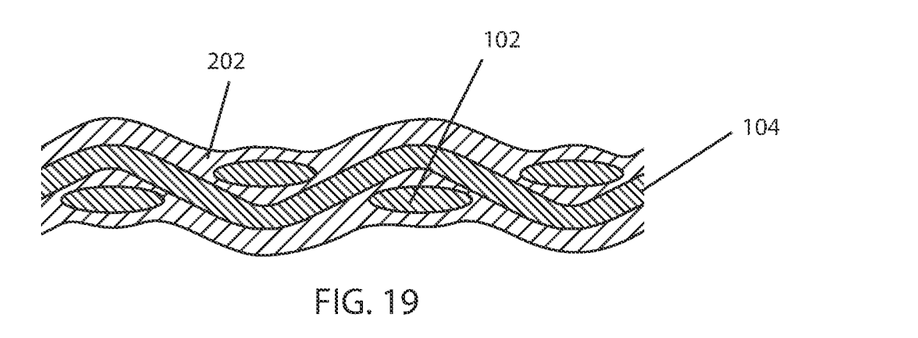
FIG. 19 is a schematic cross-sectional view of a cell encapsulation membrane as viewed along axis 3-3' of FIG. 2 in accordance with another embodiment herein.

Referring now to FIG. 19, an additional cross-sectional view is shown of cell encapsulation membrane 200 as viewed along axis 3-3' from FIG. 2 in accordance with some embodiments herein. Similar to FIG. 3, FIG. 19 shows a first series of fibers 102 and a second series of fibers 104 woven together, where the first and second series of fibers have been compressed from a circular geometry, as shown in FIG. 3, to an avoid geometry. Polymeric coating 202 is shown surrounding the mesh substrate formed by the first and second series of fibers having an ovoid shape.

It will be appreciated that domed structures can be formed in various ways. In one approach, after applying a polymeric coating onto the mesh substrate, the polymeric coating can be deformed to form the plurality of hollow domes in the apertures between adjacent fibers of the mesh substrate. For example, pressure can be applied on one side of the cell encapsulation membrane to create a pressure differential between one side of the cell encapsulation membrane and the other side in order to cause portions of the polymeric coating to deform outward, in the apertures between fibers of the mesh substrate where the polymeric coating is not reinforced by the mesh substrate fibers, forming the dome-like structures. In some embodiments, the polymeric coating can be made of a thermoplastic material and can be heated before pressure is applied. In other embodiments, the deformation can take place before a solvent used for deposition is completely evaporated.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. An implantable device comprising:
   a cell encapsulation membrane comprising
      a mesh substrate, the mesh substrate comprising
         a first series of fibers extending in a first direction and
         a second series of fibers extending in a second direction, the first series of fibers intersecting with the second series of fibers, the mesh substrate defining a plurality of apertures disposed between adjacent fibers of the first series and the second series; and a coating disposed on the mesh substrate, the coating partially occluding the plurality of apertures defined by the mesh substrate, the coating defining a central pore in each aperture in a 1:1 ratio of pores to apertures.

2. The implantable device of claim 1, the cell encapsulation membrane comprising a first cell encapsulation membrane; and a second cell encapsulation membrane;

the first cell encapsulation membrane and the second cell encapsulation membrane defining a volume there between.

3. The implantable device of claim 1, wherein the plurality of apertures disposed between adjacent fibers of the first series and second series have an average width of 5 microns to 50 microns.

4. The implantable device of claim 1, wherein the central pores have a different shape than the apertures defined by the mesh substrate.

5. The implantable device of claim 1, wherein the central pores have an average opening width of 500 nm to 5 microns.

6. The implantable device of claim 1, the central pores comprising webbed pores.

7. The implantable device of claim 1, the coating comprising a polymeric coating.

8. The implantable device of claim 7, wherein a thickness of the polymeric coating disposed over the mesh substrate varies in thickness radially around a lengthwise axis of each fiber in the first series and the second series.

9. The implantable device of claim 7, wherein a thickness of the polymeric coating disposed over the mesh substrate varies in thickness radially around a lengthwise axis of each fiber in the first series and the second series and is thicker on a side of each fiber that is between adjacent fibers than on sides of the fibers facing an outer or inner surface of the cell encapsulation membrane.

10. The implantable device of claim 7, the polymeric coating comprising a partially-fused particulate polymeric coating.

11. The implantable device of claim 7, wherein the central pores formed by the polymeric coating are aligned with the plurality of apertures defined by the mesh substrate, the polymeric coating further comprising a second set of pores that are not aligned with the apertures defined by the mesh substrate.

12. The implantable device of claim 1, the coating comprising a metal or metal oxide coating.

13. The implantable device of claim 1, the coating comprising a first polymer coating layer and a second metal or metal oxide coating layer.

14. The implantable device of claim 1, wherein an average total thickness of the mesh substrate and the coating disposed on the mesh substrate is from 50 microns to 100 microns.

15. The implantable device of claim 1, wherein the first series of fibers and second series of fibers are arranged with their lengthwise axes at an angle of about 15 degrees to 90 degrees to one another.

16. The implantable device of claim 1, wherein the first series of fibers and second series of fibers are arranged in a weave pattern with respect to one another.

17. The implantable device of claim 1, further comprising a hydrogel layer disposed over the coating on one side of the cell encapsulation membrane.

18. The implantable device of claim 17, the hydrogel layer comprising an angiogenic active agent disposed therein.

19. The implantable device of claim 18, wherein the angiogenic active agent is distributed within the hydrogel layer forming a concentration gradient with a higher concentration on an outside surface and a lower concentration on an inside surface.

* * * * *